(12) United States Patent
Attila

(10) Patent No.: US 7,820,096 B2
(45) Date of Patent: Oct. 26, 2010

(54) TURGOR SHAPING. CONTROL OF SHAPE AND RIGIDITY THROUGH THE USE OF PRESSURE TRANSMITTING CHANNEL PATTERNS (HYDRAULIC CHANNEL ARRAYS)

(76) Inventor: Mady Attila, 1450 S. Kihei Rd., Suite G104, Kihei, HI (US) 96753

( * ) Notice: Subject to any disclaimer, the term of this patent is extended or adjusted under 35 U.S.C. 154(b) by 0 days.

(21) Appl. No.: 11/868,433

(22) Filed: Oct. 5, 2007

(65) Prior Publication Data

US 2009/0092794 A1    Apr. 9, 2009

(51) Int. Cl.
B29D 22/02 (2006.01)
B29D 23/00 (2006.01)
B29D 29/00 (2006.01)
A61M 29/00 (2006.01)

(52) U.S. Cl. ......... 264/500; 264/510; 264/572; 604/96.01; 604/101.01

(58) Field of Classification Search ......... 428/166, 428/188; 604/96.01, 101.01; 137/223; 114/39.11, 114/54, 345; 417/394; 264/500, 510, 572
See application file for complete search history.

(56) References Cited

U.S. PATENT DOCUMENTS 4,103,368 A * 8/1978 Lockshaw ............... 126/566
5,370,601 A * 12/1994 Collins ..................... 600/41

* cited by examiner

*Primary Examiner*—Donald Loney

(57) ABSTRACT

Layers of materials are laminated together preserving potential spaces that can transmit pressure generated by the use of gases or fluids. Alternatively, pre-manufactured pressure conduits of suitable dimensions and geometries are integrated between the layers. Transmission of pressure to such conduits results in expansion of a compacted device to a predetermined shape. Maintenance and/or variation of said pressure results in preservation of said shape, fine static control of surface geometries and even remote control of precise movements. Osmotic Pressure is not required to achieve Turgor type control.

2 Claims, 16 Drawing Sheets

P

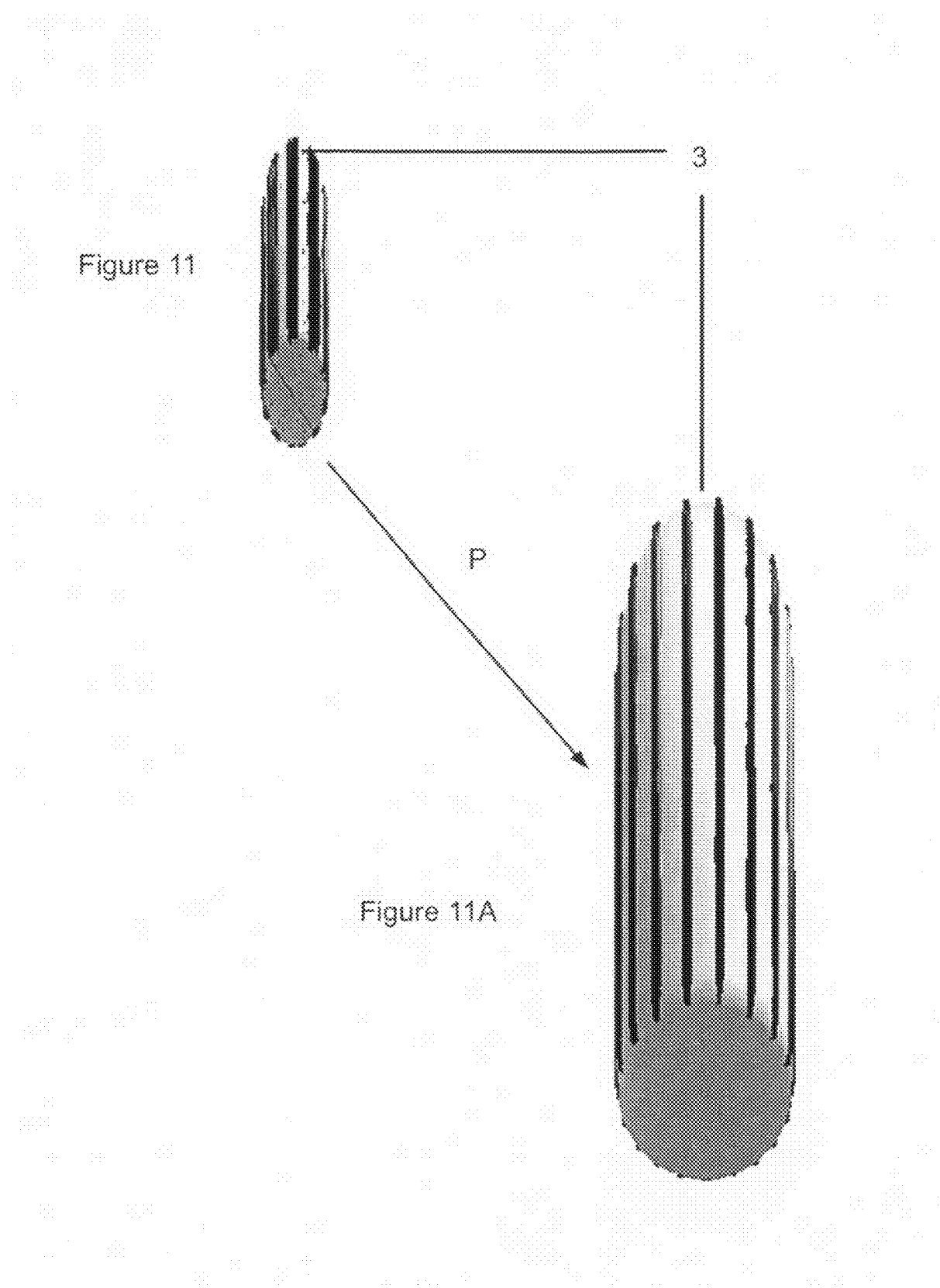

TURGOR SHAPING. CONTROL OF SHAPE AND RIGIDITY THROUGH THE USE OF PRESSURE TRANSMITTING CHANNEL PATTERNS (HYDRAULIC CHANNEL ARRAYS)

TECHNICAL FIELD

Hydraulics, laminates, memory alloys, active shape control.

BACKGROUND OF THE INVENTION

Nature teaches many invaluable lessons. Leaves expand and maintain their integrity through the use of TURGOR Pressure.

Turgor pressure is incredibly potent. It is powerful, versatile and permits absolute precision of control. Trees stay upright and maintain their structure primarily as a result of Turgor Pressure. Complex plant and leaf shapes are achieved through the use of Turgor Pressure. Life ceases without turgor pressure.

Plants achieve and control this Turgor Pressure through the regulation of solute concentrations of solutes within the conductance vessels (xylem). A greater concentration of these solutes coupled with a semi-permeable membrane that permits the free transit of water result in the production of a pressure known as Osmotic Pressure. The Osmotic Pressure of individual conductance vessels integrated over an entire structure, such as a leaf or tree, is termed Turgor Pressure.

It would be too difficult and cumbersome to replicate this complex system. However, there are many applications where this principle would be of great utility. Substitution of Osmotic type pressure with simple hydraulic pressure reduces the complexity of the system and makes practical application possible.

One situation where this technology is of use is where large devices with predominantly empty interiors are employed. Transport of such enclosures in a collapsed geometry is more economical. Houses would constitute such an application. Underwater enclosures would constitute another.

There are many applications where there is only a very limited amount of space to introduce a device. The ability to deploy such a device through the provided space without the necessity to expand this access space is useful. A gastrointestinal tube may be such an application, particularly one required for gastric lavage. Ewald tubes, as they are called, are enormous, painful and invariably cause injury during insertion. They are also life saving. The ability to introduce a small tube, but expand it into a large lumen would be of immeasurable utility.

There are many applications where devices can cause injury over time. Particularly for biological applications, the ability to only expand the devices when necessary can be of great utility. An endotracheal tube used for connecting a respirator to a patient's lung is one such application. Current endotracheal tubes employ a cuff to retain the tube within the trachea. This cuff causes necrosis over time, in some cases in as short of an interval as 72 hours. A more compliant tube with a better regulated geometry would save countless lives.

There are many applications (predominantly biological) where precise remote control of geometries is useful. There are similarly many applications where the ability to control movement, as well as the shape of a specific device is vital. Catheterization devices are such an application. The ability to steer tubes is currently achieved via the integration of wires within the lumen wall. This is incredibly expensive and cumbersome. It is also deadly, as it results in mishaps in even the best hands. And it squanders enormous luminal capacity due to dimensional overhead.

There are many applications where multiple lumens are required within the same device to permit all the requisite functions. Endoscopy equipment is such an application. The use of the turgor principle permits precise, but very low cost construction of such devices that maintain luminal diameters that are impossible with current technology.

One further unique area where turgor technology can be of great utility is in the capture and transduction of motive power. Sailboats, for example, utilize complex arrays of fixed laminates to capture the power of the wind. Precise control is achieved through the regulation of the deployment geometries of these laminates, known as sails. Hydraulic control permits selective opening and closing of different regions within a permanently deployed sail. It also permits impossibly rapid balancing of an array composing such a sail. Given the incredible cost of fuel, as well as engine maintenance, of powerboats, is envisioned that application of turgor type of construction will result in sailboats displacing powerboats as the predominant type of watercraft.

Lexicon

Turgor Pressure in common parlance is the outward pressure and tone of living tissues. This is not the original definition. The original and appropriate definition of Turgor Pressure for the purpose of this patent application is the pressure exerted within the conductance vessels ("xylem") of plants and their leaves.

Hydraulic channel is defined as a channel with sufficient structural integrity and sufficiently low compliance to transmit and maintain pressure. NOTE: hydraulic channels for the purpose of this application do NOT require the flow of fluids.

A working fluid is defined as a substance of variable shape that can transmit a pressure via a hydraulic channel. A working fluid can be a gas, liquid, plasma or other substance with the requisite characteristics.

A hydraulic channel array subsegment is the basic subunit of this invention and is defined as a complex of hydraulic channels that is interconnected in such a manner as to maintain a uniform pressure within all channels that comprise it.

Compaction ("scrunching") is defined as application of an external force to shape the device prior to deployment into the desired deployment geometry.

Dimensional overhead is defined as the difference between the effective diameter and the overall manufactured diameter of a device. For example, the dimensional diameter of an endotracheal tube is the difference between the central lumen that transmits the air and the outside diameter of the tube.

BACKGROUND ART

Extensive and exhaustive search of the USPTO and EP seach sites has revealed no prior art relevant to the current application. Specifically, there is no mention of laminate constructions to integrate hydraulic channels, nor shape control through the transmission of hydraulic pressure through such hydraulic channels, nor the generation and control of motion at a distance through the transmission of hydraulic pressure through such hydraulic pressure channels.

BRIEF SUMMARY OF THE INVENTION

Layers of materials are laminated together preserving potential spaces that can transmit pressure generated by the use of gases or fluids. Alternatively, pre-manufactured pressure conduits of suitable dimensions and geometries are integrated between the layers. Transmission of pressure to such conduits results in expansion of a compacted device to a predetermined, shape. Maintenance and/or variation of said pressure results in preservation of said shape, fine static control of surface geometries and even remote control of precise movements. Osmotic Pressure is not required to achieve Turgor type control.

DESCRIPTION OF THE DRAWINGS

FIGS. 9, 9A and 9B (Oblique 3D) illustrate one proposed procedure for manufacture of the pre-formed hydraulic skeleton required for high pressure applications. Hydraulic skeleton is manufactured through a "lost substrate" method (analogous to "lost wax" casting method). Item 4 is the hydraulic skeleton formed over the substrate (same skeleton as in FIGS. 5 through 8), Item 5 is the substrate that forms the template for the skeleton, Item 6 is the intermediate complex of hydraulic skeleton and substrate. Item A (which is a manufacturing step) is the deposition of the hydraulic skeleton over the substrate, whereas Item B is the removal of the template substrate from within the hydraulic skeleton/substrate complex. (Substrate can be removed by multiple means, such as heat, chemicals, current, electromagnetic waves, hard radiation or biological activity—see text for further clarifications of the "lost substrate" method.)

FIGS. 11 and 11A (Oblique 3D) illustrate a second application, namely expansion of a catheter after placement. Please note that the applied pressure not only permits expansion of the catheter from its pre-packaged form to its final working configuration, but also supplies rigidity. Legend as in prior figures.

FIG. 12 demonstrates a longitudinal control array, whereas FIG. 12A demonstrates a transverse control array. The pre-fabricated shape of Item 9, the control zone, determines the final geometry of the construct when pressure is applied. The control zones are controlled by Item 10, the pressure control lines, that transmit pressure to the control zones. Item 11 are equalization channels that permit uniform distribution of pressure within the control zone.

FIGS. 14A, 14B and 14C illustrate the position of the control zone within the catheter. FIG. 14A is a longitudinal side view, FIG. 14B is a longitudinal top view of a flayed out catheter and FIG. 14C is another longitudinal side view, but the catheter rotated 90 degrees leftward from view 14A. (Please note the increased density of hydraulic channels on the left side in FIG. 14C; this signifies two layers of pressure channels, one supplying background rigidity and the second providing the maneouverability. FIG. 14D shows the catheter bent under the influence of pressure. Same legend as in prior Figures. Comment: Use of multiple steering zones permits bending of catheters at pre-selected sites and in pre-selected directions.

DETAILED DESCRIPTION OF THE INVENTION

Hydraulic channel arrays are created by laminating thin layers together. These channels are achieved by preserving potential spaces that can transmit pressure generated by the use of gases of fluids. Alternatively, pre-manufactured pressure conduits (hydraulic skeletons) of suitable dimensions and geometries are integrated between the layers. Transmission of pressure to such conduits results in expansion of a compacted device to a predetermined shape. Maintenance and/or variation of said pressure results in preservation of said shape, fine static control of surface geometries and even remote control of precise movements. Osmotic Pressure is not required to achieve Turgor type control.

Turgor pressure is very potent. The overall force generated by the system is the applied pressure minus the ambient pressure, integrated over the entire surface of the hydraulic channel array. Many small vessels working together can sum to enormous pressures.

To avoid breakdown of laminates with time pre-manufactured hydraulic skeletons are envisioned (this is how nature does it). Restricting conduits to small diameters would limit forces and would impose achievable requirements for laminated and unlined conduits. Multilayer laminates give further strength and 3D rigidity.

Pre-manufactured hydraulic skeletons can easily be manufactured. A 3D printing method is used to lay down a supportive framework (substrate), which will accept the conduit forming polymer. When the desired shape is achieved, the substrate is removed (this can be achieved through physical means, such as heating—melting and/or sublimation, electricity, some form of electromagnetic radiation to break down the chemical structure of the substrate, or the use of particulate radiation; biological organisms may also be used to "eat away" the substrate). This "lost substrate" method is analogous to the "lost wax" method.

The generation and transmission of pressure does not require significant system volume capacity. Similarly, limitation of system distensibility limits the amount of fluid flow required to transmit pressure.

Gases are compressible. While there may limited applications where they are preferred, they require greater flows, are harder to control and generate complex pressure disequilibrium effects. Their use is not recommended in useful applications.

Figure 1:
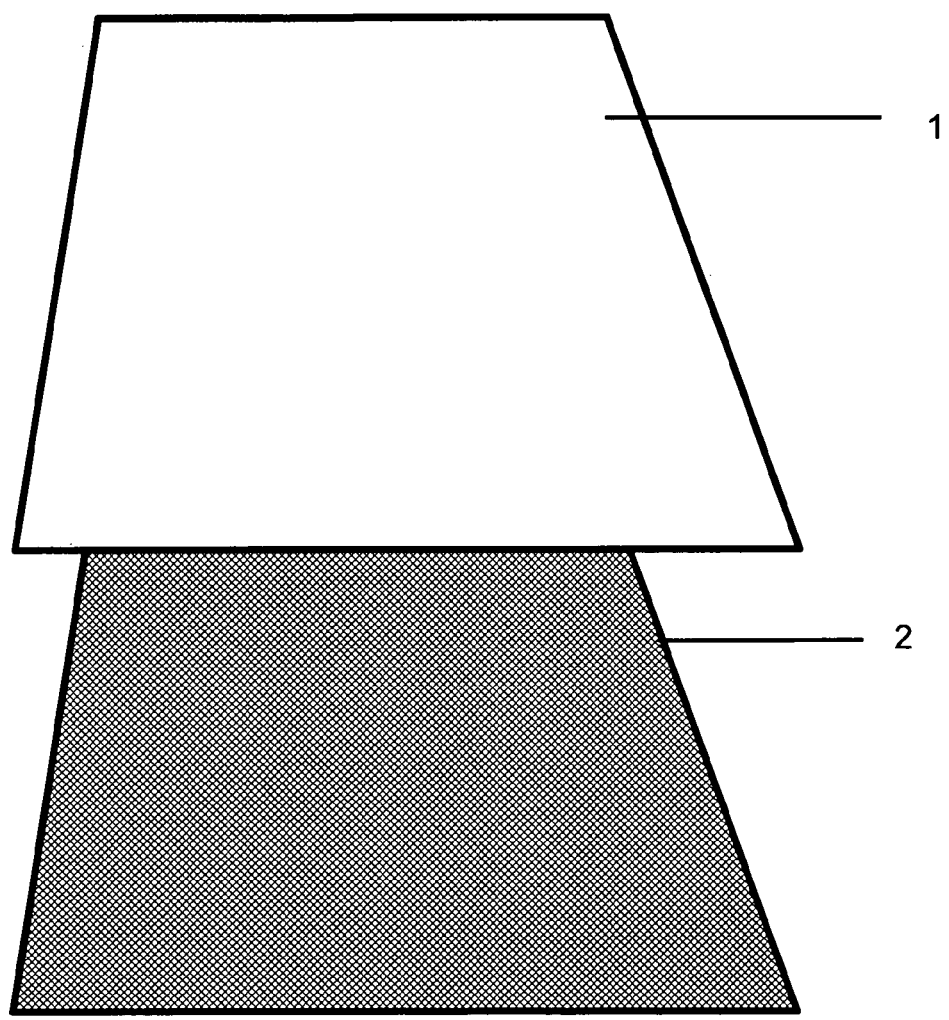
FIG. 1 (Oblique) illustrates the fundamental principle of turgor structures. There are channels cut into the mating surfaces of the two layers. When these surfaces are mated, they form communicating channels between laminated layers. Alternatively, for very low pressure applications, pre-cutting of channels is not necessary and the surfaces are simply laminated together in such a way as to leave unadhered portions that form channels. This image illustrates geometries for low pressure applications and therefore does not integrate a pre-formed hydraulic skeleton. Item 1 is the top stratum, Item 2 the bottom stratum.
Figure 2:
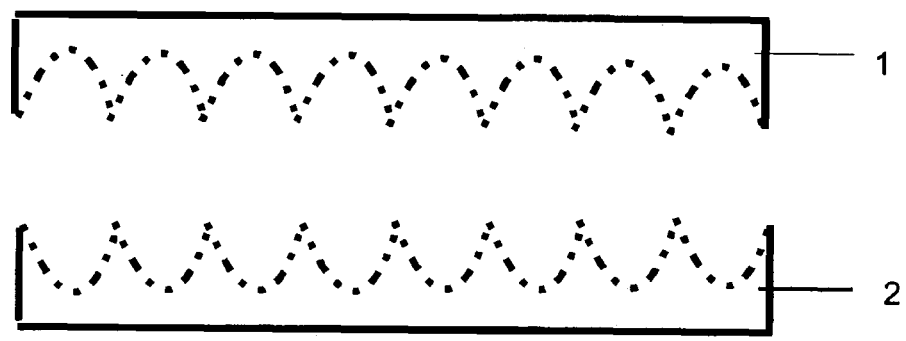
FIG. 2 (Cross Section) illustrates the geometry of the inner surfaces to be mated. There is emphasis on the pre-cut channels, but as explained above this is not a mandatory feature. Also as above, this image illustrates geometries for low pressure applications and therefore does not integrate a pre-formed hydraulic skeleton. Same legend as FIG. 1.
Figure 3:
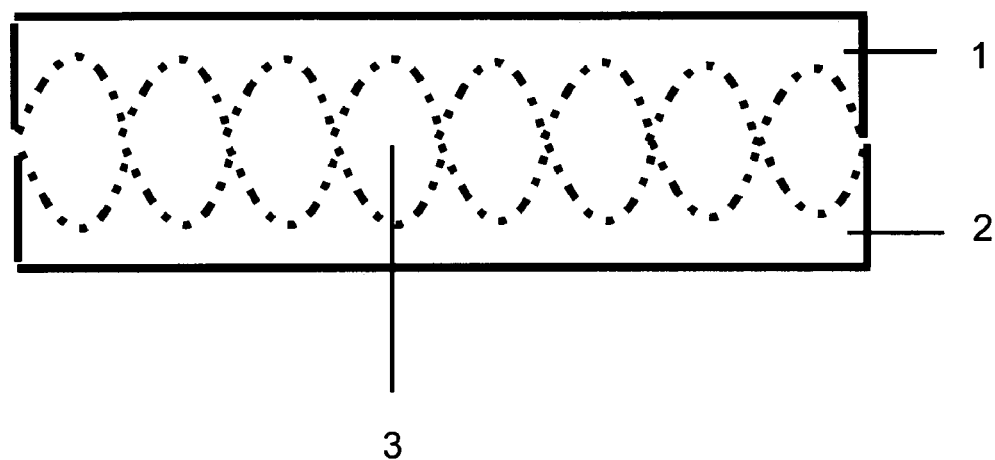
FIG. 3 (Cross Section) illustrates the nature of the intended channels. The surfaces are now bonded, forming the aforementioned channels. As above, this image illustrates geometries for low pressure applications and therefore does not integrate a pre-formed hydraulic skeleton. Same legend as FIGS. 1 and 2. Additional Item 3 is the pressure conduit.
Figure 4:
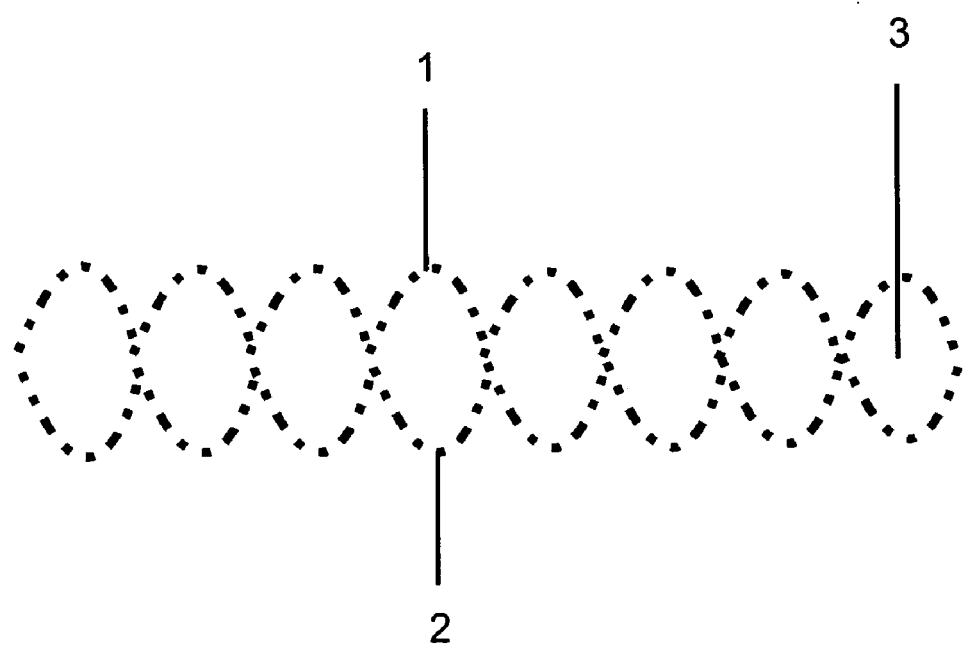
FIG. 4 (Cross Section) illustrates the flexibility of the technology in terms of adapting to various requirements. In this case, the outer surface is intentionally textured for better traction (such as in biological applications, where tissues usually excrete slippery fluids). Also, the sheets are laminated together without channels having been pre-cut (this is analogous to bubble wrap, except that the channels cells are intentionally shaped to be squeezed together when inflated). As above, this image illustrates geometries for low pressure applications and therefore does not integrate a pre-formed hydraulic skeleton. Same legend as prior figures.
Figure 5:
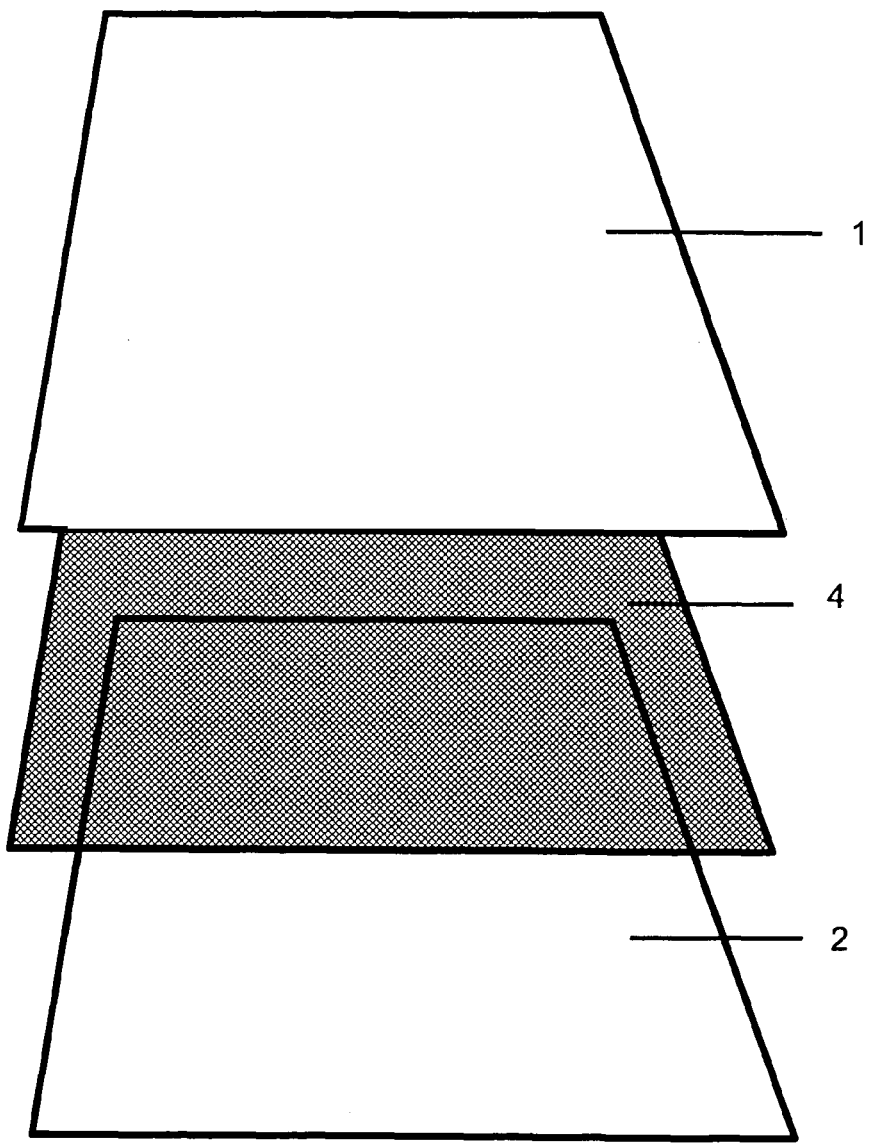
FIG. 5 (Oblique) illustrates the fundamental principle of integrating a pre-formed hydraulic skeleton between laminated layers. This image illustrates geometries for high pressure applications and does integrate the aforementioned pre-formed hydraulic skeleton. Same legend as prior figures. Please note additional Item 4, the pre-formed hydraulic skeleton.
Figure 6:
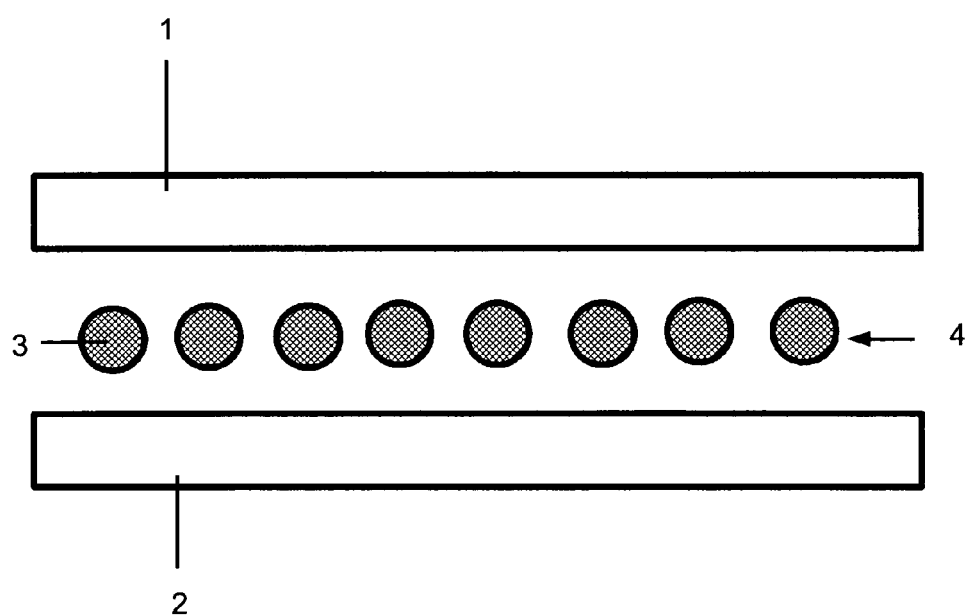
FIG. 6 (Cross Section) illustrates the geometry of the inner surfaces to be mated. As above, this image illustrates geometries for high pressure applications and does integrate a pre-formed hydraulic skeleton. Same legend as prior figures.
Figure 7:
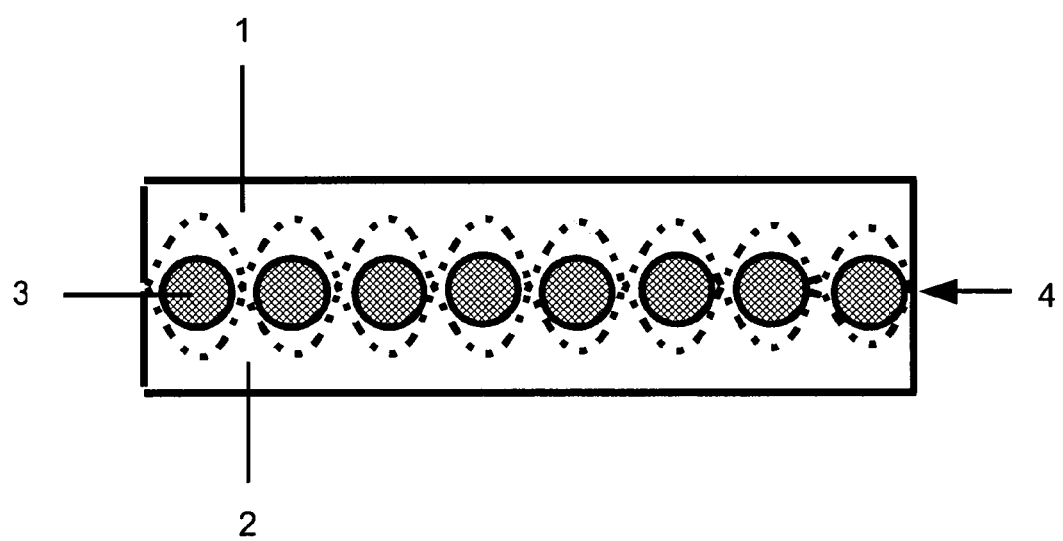
FIG. 7 (Cross Section) illustrates the nature of the channels intended. As above, this image illustrates geometries for high pressure applications and does integrate a pre-formed hydraulic skeleton. Same legend as prior figures.
Figure 8:
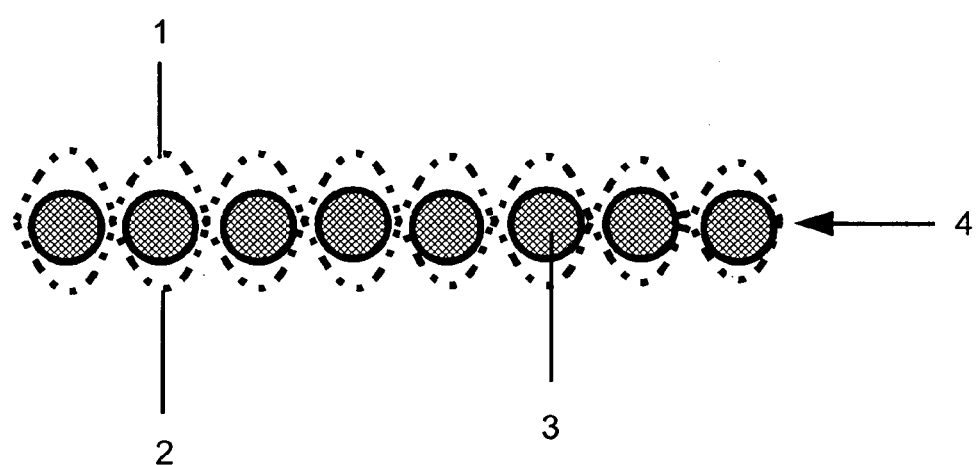
FIG. 8 (Cross Section) illustrates the flexibility of the technology in terms of adapting to various requirements. In this case, the outer surface is intentionally textured for better traction (such as in biological applications, where tissues usually excrete slippery fluids). Also, in this case the upper and lower laminate layer only serves to provide texture and enhance the integrity of the pre-formed skeleton. As above, this image illustrates geometries for high pressure applications and does integrate a pre-formed hydraulic skeleton. Same legend as prior figures.
Figure 9:
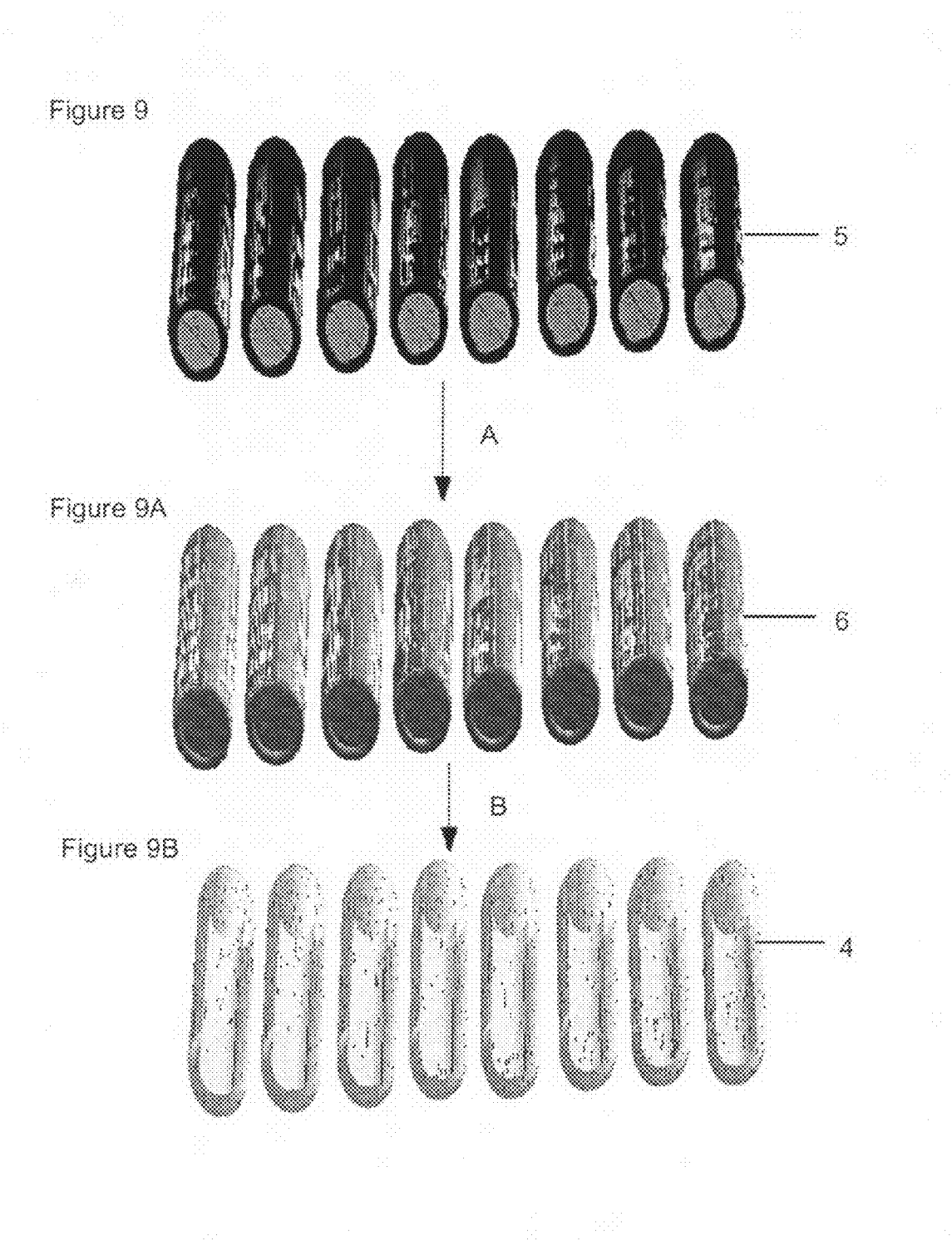
Figure 10:
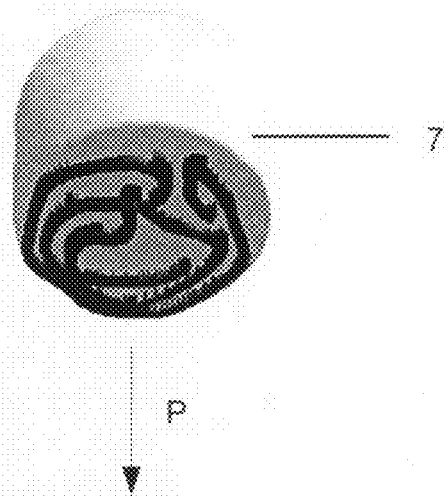
FIGS. 10 and 10A (Oblique 3D) illustrate one application, namely deployment of a compacted substrate. Item 7 is the pre-compacted item to be deployed, Item 8 is the device expanded to its working configuration by the application of pressure to the hydraulic pressure array. Item P is the application of the pressure.
Figure 10A:
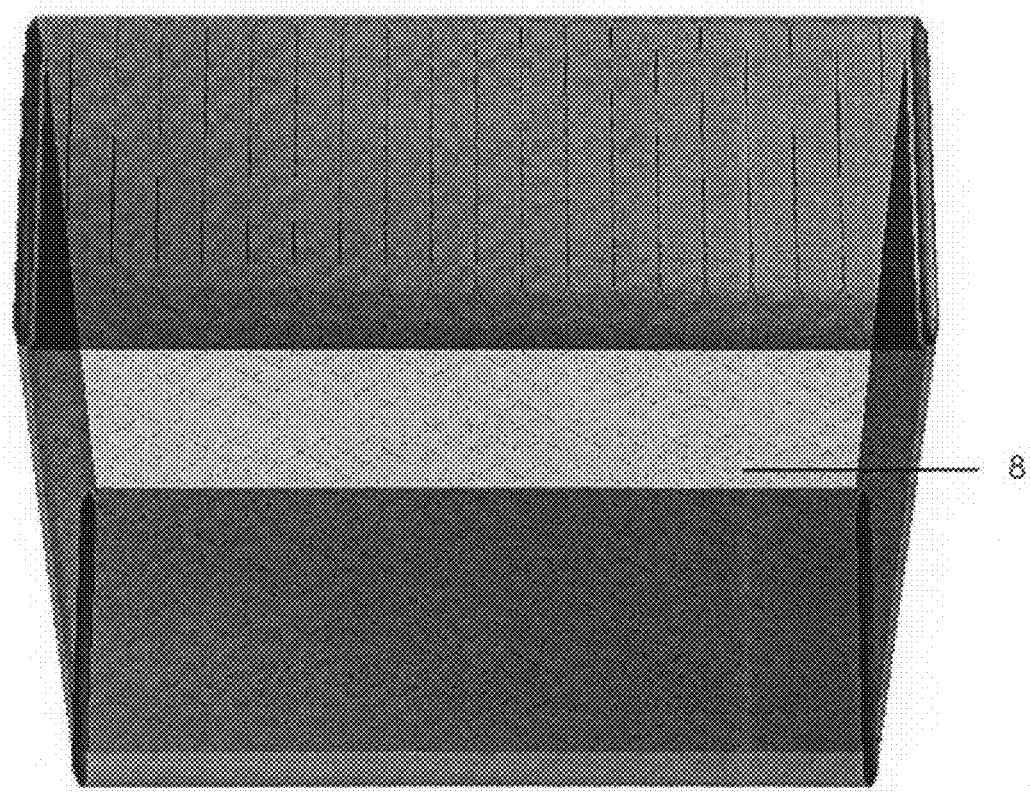
Figure 12:
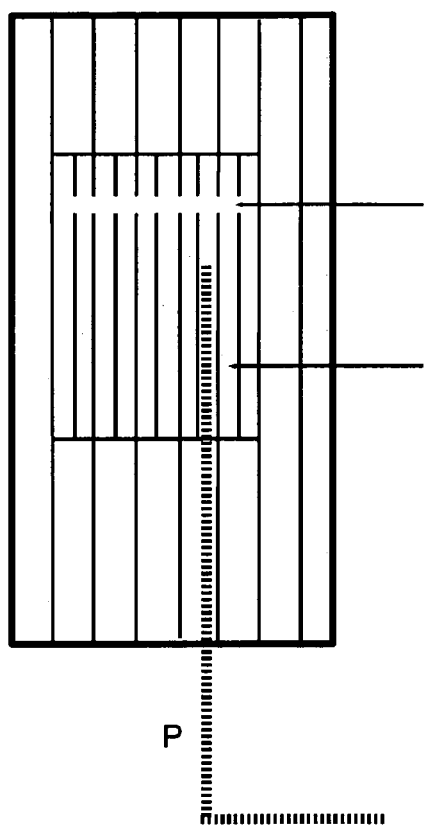
FIGS. 12 and 12A (Top) illustrates geometries to achieve shape control.
Figure 12A:
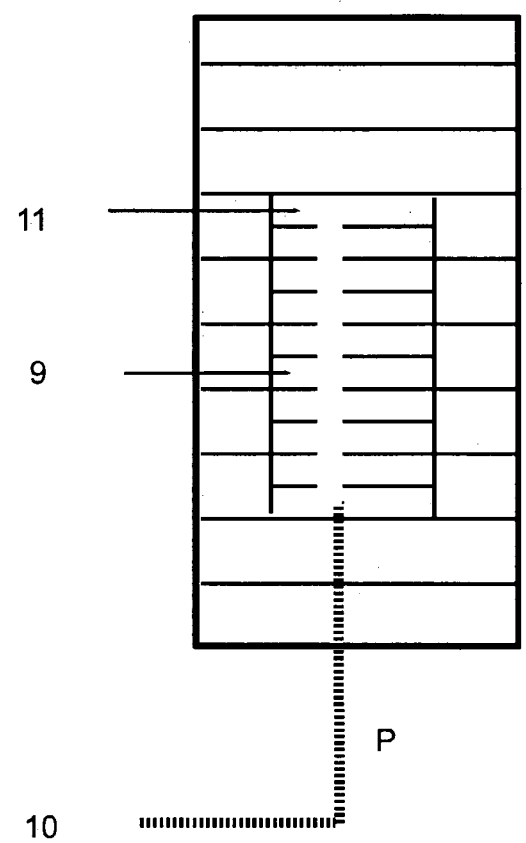
Figure 13:
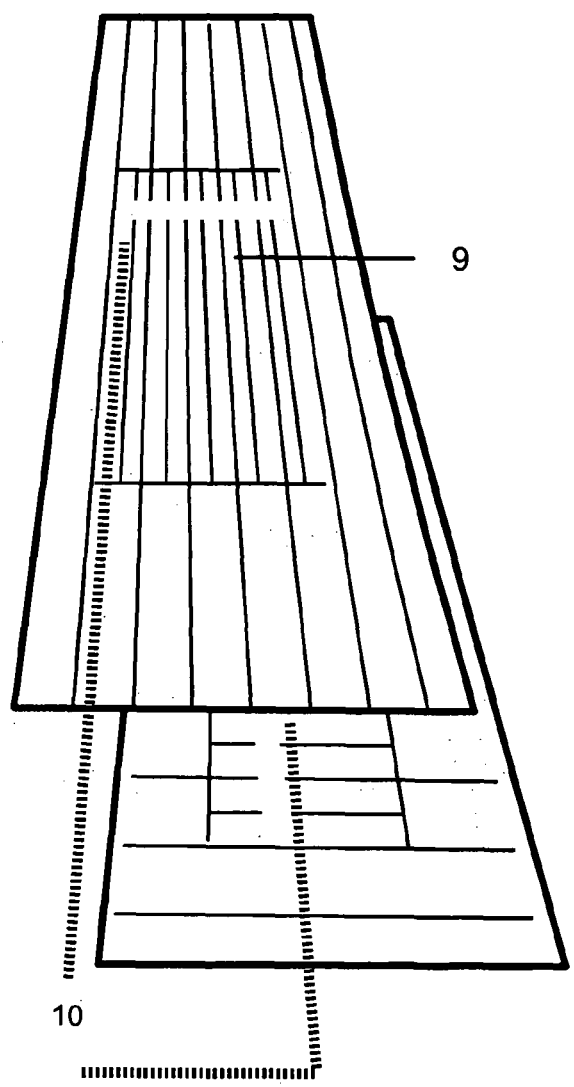
FIG. 13 (Oblique Frontal 3D) illustrates multi-layer laminates to achieve complex shape control. Two strata are illustrated; when deployed, the top layer will curve radially and the bottom will curve longitudinally. The use of multiple layers will also increase rigidity and increase the ability of the structure to resist deformation from multiple vectors. Legend is as in prior Figures.
Figure 14A:
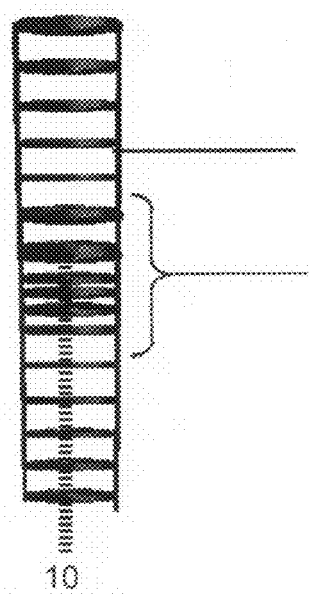
FIGS. 14A, 14B, 14C and 14D illustrate the use of shaping technology in a catheter application.
Figure 14C:
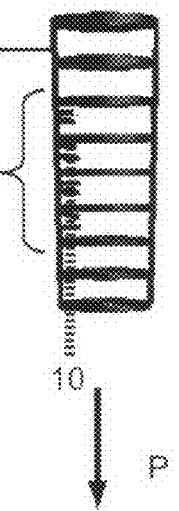
Figure 14B:
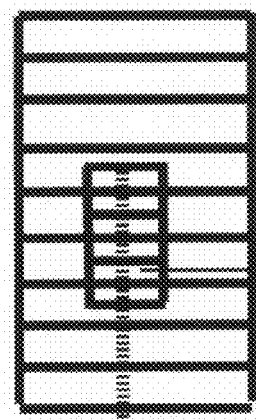
Figure 14D:
Figure 15:
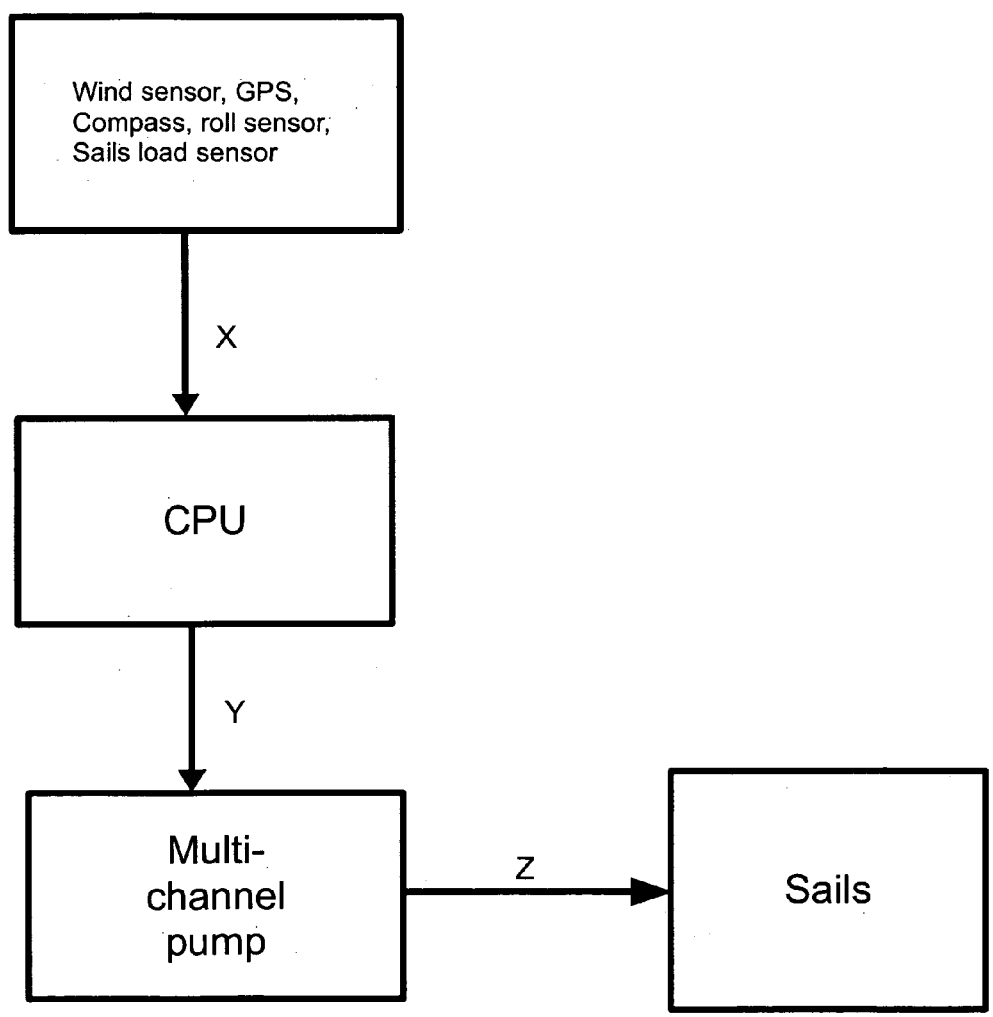
FIG. 15 (Schematic) illustrates the control logic of another application, turgor sails. A wind sensor, GPS, compass, roll sensor and sails load sensor gather data that is sent to the CPU, which regulates a multi-channel pump that selectively inflates and deflates segments of the sail. Since this is a schematic, a text box format is used. Arrow X is the transmission of sensor data, Arrow Y the transmission of CPU commands to the multi-channel pump and Arrow Z the transmission of pressure through individual hydraulic control lines to inflate and deflate segments of the sail.
Figure 16:
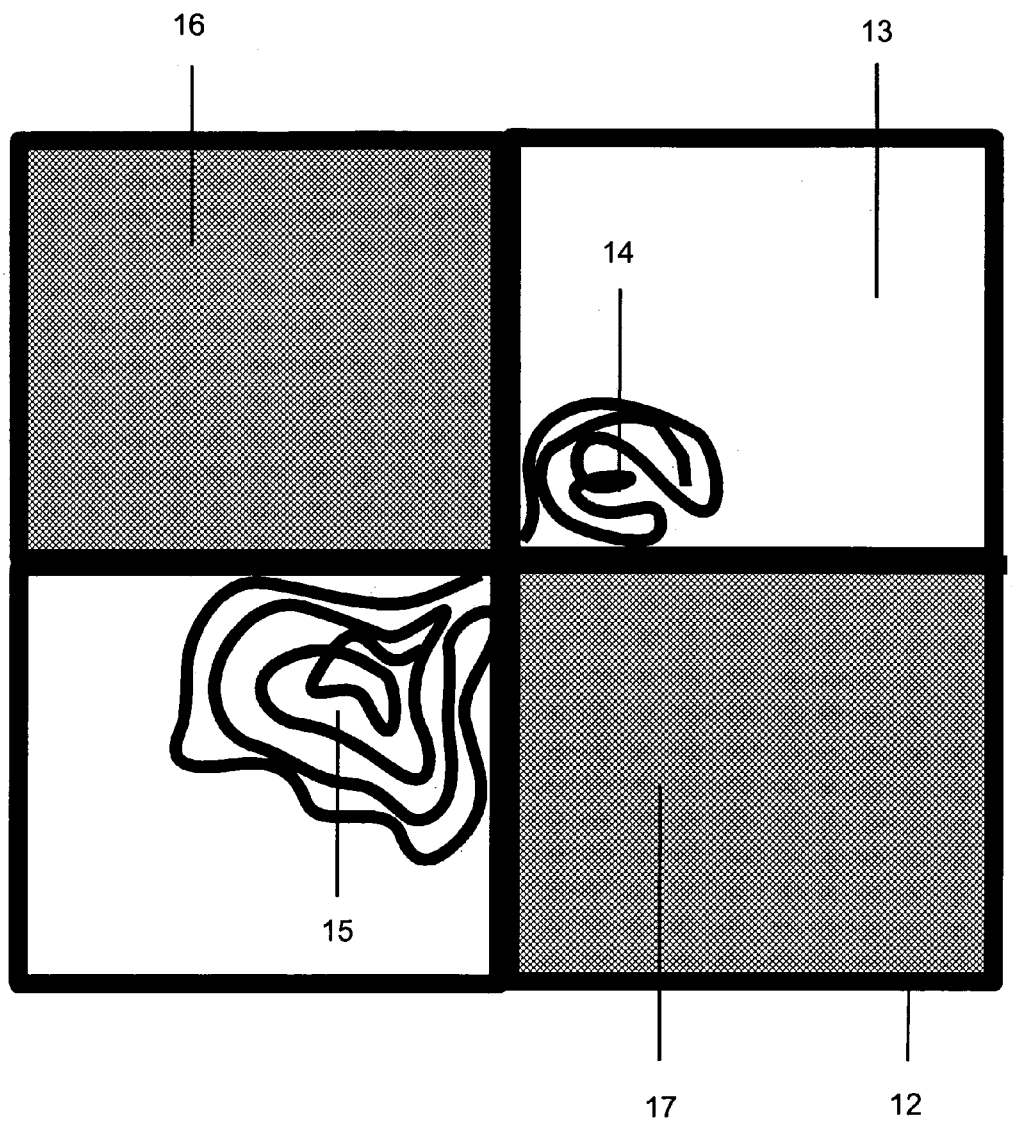
FIG. 16 (Front) illustrates the operation of a hydraulic array ("Turgor") sail. Four elements of a turgor sail in various stages of deployment are presented. Item 12 is the rigid turgor frame (which may itself be hydraulically shaped, or it could be an independently rigid or indistensible skeleton, such as a rigid metal frame or flexible Kevlar network defining a number of apertures). Item 13 is one of the aforementioned apertures, Item 14 is a compacted sail segment ("Sails down"), Item 15 is a partially expanded/tensed sail segment, Item 16 is an expanded/tensed sail segment obstructing its aperture ("Sail Unfurled") and Item 17 is the aperture obstructed and catching wind.

The regional segmentation of the overall array, either within the same layer, or in neighboring layers, can result in exquisite shape control. For instance, a catheter that is soft and flaccid without the application of pressure can be hardened into a texture approximating hard plastic or even metal through the use of longitudinal and concentric pressure lines. Further subsegmentation of the overall array, for example by application of a distensible array applied to one side of the catheter, can result in a bend at this specific location (see FIG. 8). The geometry of the printed array at this location, in turn, will determine the radius of the bend and the angle to which the catheter would want to bend without opposition.

Printed circuitry to deliver the hydraulic pressure to distant sites is easy to design. Generally, the array(s) only need commence at the location of utility. Arrays can be closely approximated, or laminated onto each other at different levels. In either case, there's always a way of getting the control pressure to the desired target and there's usually sufficient space for the required shaping hydraulic pressure array. It is theoretically possible to manipulate hundreds of individual arrays simultaneously, yet independent of each other and without interference.

Since the original device is manufactured in the shape desired after expansion, the final deployment geometry is known. Compaction ("scrunching") for the purpose of deployment is a trivial matter and only requires basic considerations, such as any limitations imposed by the means of access to the deployment site (for instance, diameter of the throat to permit the insertion of an endotracheal tube, or the diameter of a door to permit the introduction of a deflated chair into a living room).

Compaction can be precisely regulated through the use of a mold and some means of regulating the application of a force to make the construct conform to the mold during the application of compaction force. For instance, an expanded endotracheal tube can be inserted into an outer donut with elastic walls and of an appropriate diameter to accept said tube. An external pressure can then be applied on the walls of this donut, compressing the endotracheal tube into a generally cylindrical shape.

The pre-pressure geometries of the laminates, along with the pattern of the integrated hydraulic channel array cooperate to restitute very precisely the original geometry upon re-expansion. The enormous pressures possible with a large number of pressure conduits can result in impressive rigidity and structural integrity.

Complex shapes can be realized through the integration of various devices. Complex unfolding sequences means devices can be inserted into and deployed into complex spaces through small orifices. The only current technologies to remotely control shape, memory shape alloys (such as nitinol; for instance), thermostat type laminates (laminating two metals with different expansion coefficients together) and wire type techniques cannot approximate the proposed technology in terms of utility or cost efficiency.

Motion can be exquisitely controlled to various hydraulic arrays. Unlike with current technologies, dynamic motion control is possible. The individual variation and modulation of pressure within specific zones of the hydraulic channel can result in very precise shape control, as long as the external forces impeding such motion are significantly less than the steering forces.

Elimination of steering wires from the walls of catheters and endoscopic devices would reduce the dimensional overhead. This would reduce discomfort of the procedure, increase precision and yield, permit better visualization due to better irrigation, permit the access of better biopsy and other intervention devices (such as for sclerosis) and finally would permit access to sites that are currently not accessible (such as the distal small intestine, for instance)

Possibly the most remarkable potential application of this technology would be in a sailboat. Sailing vessels of unimaginable sizes would be possible through the use of this technology. Sails of square kilometer size can be modularly constructed with turgor technology. Alternatively, the control of sails suitable for personal watercraft becomes a trivial matter through the use of computer technology. A sail can be maintained on the mast under essentially all but the most vicious of gales. Apertures within the sail can be closed or opened at will by the application or release of hydraulic pressure to the individual leaflets. This would permit the elimination of most rigging and would also permit simple yet very specific feedback to guide the computer. Turgor pressure would also permit the use of much larger sails, due to increased safety and precision of control. Finally, it would demand much lower skill of the operator—a key point, given that sailing is a complex and often hazardous endeavor.

The invention claimed is:

1. A method comprising
   a) shaping a flexible substrate impermeable to a given working fluid into one or more cells capable of containing without loss said working fluid under pressure,
   b) followed by arranging said cells next to each other in a pre-determined deflated configuration defining one or more planes, spherical shells, conical shells, or any combination thereof,
   c) followed by a step selected from the group consisting of
      i) adhering each cell to its neighbors in such a fashion that inflation of said cells with said working fluid shall constrain at one or more points the initial geometry of the resultant assembly into a pre-determined deformation along the axis perpendicular to the tangent defining the aforesaid planes, spherical shells, conical shells, or any combination thereof,
      ii) applying and adhering a flexible backing membrane to said cell or cells in such a fashion that inflation of said cell or cells with said working fluid shall constrain at one or more points the initial geometry of the resultant assembly into a pre-determined deformation along the axis perpendicular to the tangent defining the aforesaid planes, spherical shells, conical shells, or any combination thereof,
      iii) and applying and adhering a flexible backing membrane to said cells in such a fashion that inflation of said cells with said working fluid shall constrain at one or more points the initial geometry of the resultant assembly into a pre-determined deformation along the axis perpendicular to the tangent defining the aforesaid planes, spherical shells, conical shells, or any combination thereof and then additionally directly adhering one or more cells to their neighbor,
   d) followed by connecting said cells via pressure conduits capable of transmitting the pressure necessary to effect the aforesaid pre-determined deformation,
   e) followed by connecting the aforesaid pressure conduits to one or more remote pressure sources capable of supplying adequate pressure to achieve the aforementioned pre-determined deformation at the target site,
   f) followed by regulating said pressure by means of a regulatory mechanism to achieve, maintain or dynamically modulate the geometry of the assembly.

2. The method of claim 1 further comprising one or more steps from the following group
   a) grouping the cells into one or more functional units arranged along one or more layers to achieve one or more geometrically distinct bends in the initial surface along a line, series of lines, a conical section, a series of conical sections, or any combination thereof, or to permit remote realization of complex shapes, or to permit precise regulation of desired shapes through generation of opposing forces at the target control site, or to permit precise movements at exact locations,
   b) pre-biasing the pressure conduits themselves either through pre-forming, or through the use of varying elastic parameters at varying points of the cell, so that when they are inflated their three dimensional geometry is altered in a direction other than radial or circumferential,
   c) using an external pressure greater than the ambient pressure within the pressure conduits and air cells of the assembly to pre-compact the assembly for deployment and then re-expand the assembly when desired to its final working geometry through the application of pressures in excess of those of the surrounding environment to the pressure conduits and air cells,
   d) the application of the method to large flat arrays for the purpose of capturing motive power from light or wind,
   e) and rolling the assembly around its longitudinal axis into a tube with one or more central lumens, with the apparatus for the control of shape integrated into the wall or walls of said catheter.

\* \* \* \* \*